United States Patent [19]

Moghe et al.

[11] Patent Number: 5,786,519
[45] Date of Patent: Jul. 28, 1998

[54] PROCESS FOR THE PREPARATION OF A MIXTURE OF GUAIACOL AND P-METHOXY PHENOL

[75] Inventors: Pramod Prabhakar Moghe; Paul Ratnasamy, both of Pune; Robert Raja, Madras; Ashwini Vinayak Pol, Pune; Madhav Gopal Kotasthane, Pune; Prakash Kondiba Bahirat, Pune, all of India

[73] Assignee: Council of Scientific & Industrial Research, New Dehli, India

[21] Appl. No.: 602,600

[22] Filed: Feb. 16, 1996

[51] Int. Cl.$^6$ ............................................. C07C 41/26
[52] U.S. Cl. ............................................. 568/629
[58] Field of Search .................................... 568/629

[56] References Cited

U.S. PATENT DOCUMENTS

| | | | |
|---|---|---|---|
| 3,662,006 | 5/1972 | Massie et al. | 260/613 |
| 3,692,842 | 9/1972 | Massie | 260/613 D |
| 3,931,295 | 1/1976 | Massie | 260/502.4 |
| 4,223,165 | 9/1980 | Jouffret | 568/771 |
| 4,301,307 | 11/1981 | Jouffret | 568/771 |
| 4,892,941 | 1/1990 | Dolphin et al. | 540/145 |
| 5,149,888 | 9/1992 | Costantini et al. | 568/771 |
| 5,160,496 | 11/1992 | Costantini et al. | 568/771 |
| 5,233,097 | 8/1993 | Nemeth et al. | 568/803 |
| 5,254,746 | 10/1993 | Costantini et al. | 568/626 |
| 5,414,153 | 5/1995 | Costantini et al. | 568/771 |

FOREIGN PATENT DOCUMENTS

| | | |
|---|---|---|
| 0 314583 | 10/1988 | European Pat. Off. . |
| 0 548807 | 12/1992 | European Pat. Off. . |

*Primary Examiner*—Allen J. Robinson
*Assistant Examiner*—Barbara Badio
*Attorney, Agent, or Firm*—Greenlee, Winner and Sullivan, P.C.

[57] ABSTRACT

An improved process is provided for the preparation of a mixture of guaiacol and p-methoxy phenol which comprises reacting anisole with hydrogen peroxide in the presence of a solid catalyst containing an organotransition metal complex wherein some or all of the hydrogen atoms of the said organotransition metal complex have been substituted by one or more electron withdrawing groups, and isolating the mixture of guaiacol and p-methoxy phenol formed.

14 Claims, No Drawings

1

PROCESS FOR THE PREPARATION OF A MIXTURE OF GUAIACOL AND P-METHOXY PHENOL

FIELD OF THE INVENTION

This invention relates to an improved process for the preparation of a mixture of guaiacol and p-methoxy phenol. More particularly the present invention relates to an improved process for the preparation of a mixture of guaiacol and p-methoxy phenol by the hydroxylation of anisole, using hydrogen peroxide as the oxidant and a catalyst containing a solid organotransition metal complex.

BACKGROUND OF THE INVENTION

In terms of quantity and scope of application, guaiacol and p-methoxy phenol have found wide application in the field of medicinal organic, synthetic perfumes, anti-oxidants and polymerization inhibitors.

Two routes have gained industrial importance for the production of guaiacol, namely, methylation of catechol with dimethyl, sulphate or carbonate in the presence of alkali. For p-methoxy phenol, the known industrial route, is selective methylation of hydroquinone with dimethyl sulphate or carbonate.

There have been many references in the prior art for the manufacture of mixtures of guaiacol and p-methoxy phenol but of particular interest with respect to the present invention are processes in which aromatic compounds are hydroxylated using hydrogen peroxide as the oxidant. U.S. Pat. 3,662,006 describes a process where benzene derivatives were ring hydroxylated by a reaction with hydrogen peroxide using iron, chromium and nickel as the catalysts to get a mixture of hydroxybenzene derivatives U.S. Pat. 3,931, 295 describes the hydroxylation of aromatic compounds with hydrogen peroxide containing a salt of hydrocyanic acid or an aliphatic nitrile compound. German Patent 2,633, 302 describes a process where anisole is hydroxylated with hydrogen peroxide in $CF_3SO_3H$ containing small amounts of $H_3PO_4$. European Patent EP 314,583 describes a process where phenolic ethers and phenol derivatives were hydroxylated with hydrogen peroxide in the presence of acidic clays. European Patent EP 548,807 describes the hydroxylation of anisole with hydrogen peroxide in the presence of titanosilicate catalysts and cyclic ethers like THF, dioxan, etc.

There are many drawbacks in the existing processes mentioned hereinabove and in commercial practice worldwide. One major drawback in the preparation of guaiacol and p-methoxy phenol is the use of costly raw materials like catechol and hydroquinone. Further, methylation of phenols involves separation of products from the reaction mixture, which is also costly. Since the boiling points of several compounds are very close to each other, it is difficult to maintain strict purity requirements. The drawbacks of other hydroxylation processes mentioned in the literature are the hazardous reaction conditions of the processes, use of expensive corrosive liquid catalysts like HF, $CF_3COOH$, HF complexes, use of drastic conditions e.g. reaction at $-10°$ to $-70°$ C. and finally poor conversion to the hydroxylation products. An additional major drawback of prior art processes using methylating agents like dimethyl sulphate or carbonate is the need to dispose of reaction byproducts like sodium sulphate or carbonates, which are generated when the reaction mixture is neutralized with alkali to isolate guaiacol and p-methoxy phenol.

There is, thus, a need for the development of a process for the hydroxylation of anisole, a rather cheap starting material, to guaiacol and p-methoxy phenol in significant yields and using solid recyclable catalyst and operating at low enough temperatures (below 100° C.) to minimize production of side products avoiding hazardous reaction conditions.

It is therefore an object of the present invention to provide an improved process for the preparation of a mixture of guaiacol and p-methoxy phenol by the hydroxylation of anisole using a catalyst containing an organotransition metal complex which would remain in the solid state at the end of hydroxylation reaction thereby facilitating the easy separation, recovery and recycling of the catalyst from the reaction products without having any adverse impact on the environment. Another object of the present invention is to provide an improved process whereby the yield of guaiacol would be higher, selective, than in the prior art processes. Yet another objective of the present invention is to provide an improved process for the preparation of a mixture of guaiacol and p-methoxy phenol at reaction conditions wherein a large number of byproducts may be minimized.

SUMMARY OF THE INVENTION

Phthalocyanines consist of large, planar, conjugated, ring systems which serve as tetradentate ligands. Metallic cautions can be easily accommodated at the center of these systems with the four nitrogens as the ligating atoms. Metal containing phthalocyanine compounds are known to be useful as chemical reagents of a catalytic nature, more particularly in directing certain oxidative processes. Many known phthalocyanines have been judged to suffer certain drawbacks by being deficient in the combination of properties desired for many candidate uses, such as in the oxidation of aromatics and more particularly in the hydroxylation of anisole. One major drawback of homogeneous phthalocyanine catalysts in industrial oxidation processes is the formation of aggregates in solution which significantly deactivates these catalysts.

Due to our continued research in this area we observed that the organotransition metal complexes used are solids insoluble in anisole or the reaction products arising from the hydroxylation of anisole. Hence they do not undergo aggregation or change of phase during the hydroxylation wherein such changes are known to lead to catalyst deactivation problems.

Another drawback of phthalocyanines used in the prior art as catalysts for alkane oxidation is their low oxidative stability which is due to the easy oxidizability of the hydrogen atoms attached to the nucleus of the phthalocyanines.

We have found that the oxidative stability as well as the catalytic activity of the metal phthalocyanines used to catalyze the hydroxylation of anisole are enhanced by replacing the hydroqens of the phthalocyanines with electron withdrawing groups like the halogens, nitro or cyano groups thereby rendering the metal ions easier to reduce leading to an improved oxidation activity and stability of the organotransition metal complexes during the reaction.

There are a total of 16 hydrogen atom positions on such phthalocyanine molecules which can, in principle, be substituted by other substituents. We have observed that when some or all of the hydrogen atoms of the said phthalocyanines are substituted by one or more electron withdrawing groups such as halogen, nitro or cyano groups or mixtures of such groups there is substantial improvement in selectivity and conversion to yield a mixture of guaiacol and p-methoxy phenol.

Accordingly, the present invention provides an improved process for the preparation of a mixture of guaiacol and p-methoxy phenol which comprises reacting anisole with hydrogen peroxide in the presence of a solid catalyst consisting of an organotransition metal complex wherein some or all of the hydrogen atoms of the said organotransition metal complex have been substituted by one or more electron withdrawing groups, at a temperature in the range of 20° C. to 85° C., and isolating the mixture of guaiacol and p-methoxy phenol formed by conventional methods.

DETAILED DESCRIPTION OF THE PREFERRED EMBODIMENTS

In an embodiment of the present invention the organotransition metal complex is selected from phthalocyanines and porphyrins.

In another embodiment of the present invention, the transition metal is selected from iron, cobalt, copper, nickel or mixtures thereof.

Some nonlimiting examples of such organotransition metal complexes used as catalysts in the hydroxylation of anisole to a mixture of guaiacol and p-methoxy phenol are iron halo phthalocyanines, copper halo phthalocyanines, cobalt halo phthalocyanines, nickel halo phthalocyanines, iron nitro phthalocyanines, copper nitro phthalocyanines, nickel nitro phthalocyanines, cobalt nitro phthalocyanines, nickel cyano phthalocyanines, copper cyano phthalocyanines and cobalt cyano phthalocyanines.

In yet another embodiment of the present invention the electron withdrawing groups attached to the organotransition metal complex are selected from the halogens, fluorine, chlorine, bromine or iodine, or the nitro or cyano groups.

In a preferred embodiment of the present invention, the hydroxylation of anisole by hydrogen peroxide is catalyzed by the halogen, cyano or nitro phthalocyanines of the metals iron, cobalt, copper and nickel.

In yet another embodiment of the present invention, the above mentioned hydroxylation reaction can be carried out in the presence or absence of solvents. It may be an advantageous option to carry out the said oxidation reaction in the presence of a suitable solvent, thereby facilitating the separation of the said guaiacol and p-methoxy phenols from the solid catalysts. Suitable solvents for such use include acetonitrile, methanol, water, butanol and cyclohexanol. Examples of such solvents which can be used in the process of the present invention include acetonitrile, acetone, benzene or any other organic solvent which is inert under the hydroxylation reaction conditions.

In yet another advantageous embodiment of the present invention, the organotransition metal complex may be encapsulated in a solid matrix. Due to the greater dispersion of the organotransition metal complex in solid matrices and the consequent enhanced stability of the structural integrity of the catalyst, significant process advantages like greater activity, stability and easy recovery and recyclability of the catalyst are observed. Examples of such solid matrices include inorganic oxides like silica, alumina, molecular sieves, zeolites and the like as well as organic polymeric material.

It is an advantageous feature of the process of the present invention that due to the high activity of the catalysts used herein, the hydroxylation reaction can be carried out at temperatures much below those used in the prior art and preferably below 80° C., thereby leading too much lower yields of undesired side products.

The details of the present invention are described in the examples given below which are provided by way of illustration only and therefore should not be construed to limit the scope of the invention.

EXAMPLE 1

A 250 ml 4 necked flask fitted with stirrer, condenser, thermometer, and addition funnel in an electrically heated oil bath was charged with 0.5 g of solid copper tetra deca chloro phthalocyanines, acetonitrile 50 ml (39 g) and anisole 11.5 g. Hydrogen peroxide 13.6 ml (28%) (3.808 g) was slowly added dropwise at 50° to the reaction mixture under stirring in 30 minutes. The reaction was continued at 80° for 8 hrs. The reaction mixture was then cooled and separated from solid catalyst by centrifugation and analyzed by gas chromatography (Hewlett Packard 5880 A) using a capillary column (50×0.25 mm, crosslinked methyl silicone gum) and flame ionization detecter (FID). The identity of the product was confirmed by GC mass spectroscopy (Shimadzu GCMS-QP 2000A) using standard compounds.

The conversion of anisole was 23.3%

The yield of guaiacol was 15.12%

The yield of p-methoxy phenol was 7.9%

EXAMPLE 2

A 250 ml 4 necked flask fitted with stirrer, condenser, thermometer, and addition funnel in an electrically heated oil bath was charged with 0.5 g of solid copper tetra deca chloro pthalocyanine, methanol 150 ml (118 g) and anisole 11.5 g. Hydrogen peroxide 13.6 ml (28%) (3.808 g) was slowly added dropwise at 50° to the reaction mixture under stirring in 30 minutes. The reaction continued at 80° for 5 hrs. The reaction mixture was then cooled and separated from solid catalyst by filtration and analysed by gas chromatography (Hewlett Packard 5880 A) using capillary column (50×0.25 mm, crosslinked methyl silicone gum) and flame ionisation detecter (FID). The identity of the product was confirmed by GC mass spectroscopy (Shimadzu GCMS-QP 2000A) using standard compounds.

The conversion of anisole was 16.75%

The yield of guaiacol was 14.4%

The yield of p-methoxy phenol was 2.1%

EXAMPLE 3

A 250 ml 4 necked flask fitted with stirrer, condenser, thermometer, and addition funnel in an electrically heated oil bath was charged with 0.5 g of solid cobalt tetra deca chloro phthalocyanines, acetonitrile 50 ml (39 g) and anisole 11.5 g. Hydrogen peroxide 13.6 ml (28%) (3.808 g) was slowly added dropwise at 50° to the reaction mixture under stirring in 30 minutes. The reaction continued at 80° for 5 hrs. The reaction mixture was then cooled and separated from solid catalyst by filtration and analyzed by gas chromatography (Hewlett Packard 5880 A) using capillary column (50×0.25 mm, crosslinked methyl silicone gum) and flame ioniSation detecter (FID). The identity of the product was confirmed by GC mass spectroscopy (Shimadzu GCMS-QP 2000A) using standard compounds.

The conversion of anisole was 19.85%

The yield of guaiacol was .14.35%

The yield of p-methoxy phenol was 4.2%

EXAMPLE 4

A 250 ml 4 necked flask fitted with stirrer, condenser, thermometer, and addition funnel in an electrically heated oil bath was charged with 1.25 g of solid nickel tetra nitro phthalocyanines encapsulated in the aluminosilicate molecular sieve-Y, acetonitrile 50 ml (39 g) and anisole 11.5 g. Hydrogen peroxide 13.6 ml (28%) (3.808 g) was slowly added dropwise at 50° to the reaction mixture under stirring in 30 minutes. The reaction continued at 80° for 5 hrs. The reaction mixture was then cooled and separated from solid catalyst by filtration and analyzed by gas chromatography (Hewlett Packard 5880 A) using capillary column (50×0.25 mm, crosslinked methyl silicone gum) and flame ionisation detector (FID). The identity of the product was confirmed by GC mass spectroscopy (Shimadzu GCMS-QP 2000A) using standard compounds.

The conversion of anisole was 15.8%

The yield of the mixture of guaiacol and p-methoxy phenol was 13.88%.

EXAMPLE 5

In a 250 ml 4 necked flask fitted with stirrer, condenser, thermometer, and addition funnel in an electrically heated oil bath was charged with 1.25 g of solid copper tetra deca chloro phthalocyanines encapsulated in the aluminosilicate molecular sieve-X, (designated as $CuCl_{14}Pc$-X, acetonitrile 50 ml (39 g) and anisole 11.5 g. Hydrogen peroxide 13.6 ml (28%) (3.808 g) was slowly added dropwise at 50° to the reaction mixture under stirring in 30 minutes. The reaction continued at 80° for 5 hrs. The reaction mixture was then cooled and separated from solid catalyst by filtration and analyzed by gas chromatography (Hewlett Packard 5880 A) using capillary column (50×0.25 mm, crosslinked methyl silicone gum) and flame ionisation detecter (FID). The identity of the product was confirmed by GC mass spectroscopy (Shimadzu GCMS-QP 2000A) using standard compounds.

The conversion of anisole was 21.6%

The yield of guaiacol was 19.4%

The yield of p-methoxy phenol was 2.1%

EXAMPLE 6

A 250 ml 4 necked flask fitted with stirrer, condenser, thermometer, and addition funnel in an electrically heated oil bath was charged with 1.25 g of solid iron tetra deca chloro phthalocyanines. encapsulated in the aluminosilicate molecular sieve-Y, acetonitrile 50 ml (39 g) and anisole 11.5 g. Hydrogen peroxide 13.6 ml (28%) (3.808 g) was slowly added dropwise at 50° to the reaction mixture under stirring in 30 minutes. The reaction continued at 80° for 5 hrs. The reaction mixture was then cooled and separated from solid catalyst by filtration and analyzed by gas chromatography (Hewlett Packard 5880 A) using capillary column (50×0.25 mm, crosslinked methyl silicone gum) and flame ionisation detector (FID). The identity of the product was confirmed by GC mass spectroscopy (Shimadzu GCMS-QP 2000A) using standard compounds.

The conversion of anisole was 22.25%

The yield of guaiacol was 20.5%

The yield of p-methoxy phenol was 1.1%

EXAMPLE 7

A 250 ml 4 necked flask fitted with stirrer, condenser, thermometer, and addition funnel in an electrically heated oil bath was charged with 0.5 g of solid copper tricyano phthalocyanines encapsulated in the aluminosilicate molecular sieve-Y, acetonitrile 50 ml (39 g) and anisole 11.5 g. Hydrogen-peroxide 13.6 ml (28%)(3.808 g) was slowly added dropwise at 50° to the reactive mixture under stirring in 30 minutes. The reaction continued at 80° for 5 hrs. The reaction mixture was then cooled and separated from solid catalyst by filtration and analySed by gas chromatography (Hewlett Packard 5880 A) using capillary column (50×0.25 mm, crosslinked methyl silicone gum) and flame ionisation detector (FID). The identity of the product was confirmed by GC mass spectroscopy (Shimadzu GCMS-QP 2000A) using standard compounds.

The conversion of anisole was 27%

The yield of guaiacol was 19.5%

The yield of p-methoxy phenol was 6.1%

EXAMPLE 8

A 250 ml 4 necked flask fitted with stirrer, condenser, thermometer, and addition funnel in an electrically heated oil bath was charged with 0.75 g of solid copper tetra nitro chloro phthalocyanines encapsulated in the aluminosilicate molecular sieve-X, acetonitrile 50 ml (39 g) and anisole 11.5 g. Hydrogen peroxide 13.6 ml (28%) (3.808 g) was slowly added dropwise at 50° to the reaction mixture under stirring in 30 minutes. The reaction continued at 80° for 5 hrs. The reaction mixture was then cooled and separated from solid catalyst by filtration and analyzed by gas chromatography (Hewlett Packard 5880 A) using capillary column (50×0.25 mm, crosslinked methyl silicone gum) and flame ionisation detecter (FID). The identity of the product was confirmed by GC mass spectroscopy (Shimadzu GCMS-QP 2000A) using standard compounds.

The conversion of anisole was 12.1%

The yield of guaiacol was 6.4%

The yield of p-methoxy phenol was 3.8%

EXAMPLE 9

A 250 ml 4 necked flask fitted with stirrer, condenser, thermometer, and addition funnel in an electrically heated oil bath was charged with 1.5 g of solid copper hexachloro tetra phenyl porphyrin encapsulated in the aluminosilicate molecular sieve-Y, acetonitrile 50 ml (39 g) and anisole 11.5 g. Hydrogen peroxide 13.6 ml (28%) (3.808 g) was slowly added dropwise at 50° to the reaction mixture under stirring in 30 minutes. The reaction continued at 80° for 5 hrs. The reaction mixture was then cooled and separated from solid catalyst by filtration and analysed by gas chromatography (Hewlett Packard 5880 A) using capillary column (50×0.25 mm, crosslinked methyl silicone gum) and flame ionisation detecter (FID). The identity of the product was confirmed by GC mass spectroscopy (Shimadzu GCMS-QP 2000A) using standard compounds.

The conversion of anisole was 13.6%

The yield of guaiacol was 9.6%

The yield of p-methoxy phenol was 3.0%

EXAMPLE 10

A 250 ml 4 necked flask fitted with stirrer, condenser, thermometer, and addition funnel in an electrically heated oil bath was charged with 1.25 g of solid $CuCl_{14}Pc$-X encapsulated in a polystyrene polymer matrix, acetonitrile 50 ml (39 g) and anisole 11.5 g. Hydrogen peroxide 13.6 ml (28%) (3.808 g) was slowly added dropwise at 50° to the reaction mixture under stirring in 30 minutes. The reaction continued at 80° for 5 hrs. The reaction mixture was then cooled and separated from solid catalyst by filtration and analysed by gas chromatography (Hewlett Packard 5880 A)

using capillary column (50×0.25 mm, crosslinked methyl silicone gum) and flame ionisation detecter (FID). The identity of the product was confirmed by GC mass spectroscopy (Shimadzu GCMS-QP 2000A) using standard compounds.

The conversion of anisole was 15.9%

The yield of guaiacol was 8.7%

The yield of p-methoxy phenol was 6.9%

EXAMPLE 11

A 250 ml 4 necked flask fitted with stirrer, condenser, theremometer, and addition funnel in an electrically heated oil bath was charged with 1.25 g of solid copper tetra deca chloro phthalocyanines encapsulated in a polystyrene polymer matrix, acetonitrile 50 ml (39 g) and anisole 11.5 g, Hydrogen peroxide 13.6 ml (28%) (3.808 g) was slowly added dropwise at 50° to the reaction mixture under stirring in 30 minutes. The reaction continued at 80° for 5 hrs. The reaction mixture was then cooled and separated from solid catalyst by filtration and analysed by gas chromatography (Hewlett Packard 5880 A) using capillary column (50×0.25 mm, crosslinked methyl silicone gum) and flame ionisation detecter (FID). The identity of the product was confirmed by GC mass spectroscopy (Shimadzu GCMS-QP 2000A) using standard compounds.

The conversion of anisole was 17.1%

The yield of guaiacol was 9.6%

The yield of p-methoxy phenol was 6.9%

We claim:

1. A process for the preparation of a mixture of guaiacol and p-methoxy phenol which comprises reacting anisole with hydrogen peroxide in the presence of a solid organotransition metal complex selected from the group consisting of phthalocyanines and porphyrins, wherein some or all of the hydrogen atoms of the said organotransition metal complex have been substituted by one or more electron withdrawing groups selected from the group consisting of halogens, the nitro group, the cyano group, and mixtures thereof, and wherein said organotransition metal complex is insoluble in reaction solvents, at a temperature in the range of about 20° C. to about 85° C., and isolating the mixture of guaiacol and p-methoxy phenol formed.

2. The process of claim 1 wherein the organotransition metal complex is a phthalocyanine.

3. The process of claim 1 wherein the organotransition metal complex is a porphyrin.

4. The process of claim 1 wherein the transition metal is selected from the group consisting of iron, cobalt, copper, nickel and mixtures thereof.

5. The process of claim 1 wherein the reaction between anisole and hydrogen peroxide is carried out in the presence of solvents.

6. The process of claim 5 wherein the solvents are selected from the group consisting of acetonitrile, methanol, butanol, acetone, and mixtures thereof.

7. The process of claim 1 wherein the organotransition metal complex is encapsulated in a solid matrix.

8. The process of claim 7 wherein the solid matrix used is an inorganic oxide selected from the group consisting of silica, alumina, aluminosilicates and molecular sieves.

9. The process of claim 7 wherein the solid matrix is an organic polymer.

10. A process for the preparation of a mixture of guaiacol and p-methoxy phenol which comprises reacting anisole with hydrogen peroxide in the presence of a solid organotransition metal complex selected from the group consisting of phthalocyanines and porphyrins, wherein some or all of the hydrogen atoms of the said organotransition metal complex have been substituted by one or more electron withdrawing groups, wherein said organotransition metal complex is encapsulated in a solid organic polymer matrix, and wherein said organotransition metal complex is insoluble in reaction solvents, at a temperature in the range of about 20° C. to about 85° C., and isolating the mixture of guaiacol and p-methoxy phenol formed.

11. The process of claim 10 wherein said matrix also comprises an inorganic oxide.

12. The process of claim 10 wherein the reaction between anisole and hydrogen peroxide is carried out in the presence of solvents selected from the group consisting of acetonitrile, methanol, butanol, acetone and mixtures thereof.

13. The process of claim 10 wherein said electron withdrawing groups are selected from the group consisting of halogens, the nitro group, the cyano group, and mixtures thereof.

14. The process of claim 10 wherein said organotransitional metal complex comprises a transition metal selected from the group consisting of iron, cobalt, copper, nickel and mixtures thereof.

* * * * *